(12) United States Patent
Loori et al.

(10) Patent No.: US 7,540,283 B2
(45) Date of Patent: Jun. 2, 2009

(54) HYPERBARIC OXYGEN DEVICES AND DELIVERY METHODS

(75) Inventors: Phillip Loori, Farmingdale, NJ (US); George Hovorka, East Boston, MA (US)

(73) Assignee: AOTI, Inc., Tamarac, FL (US)

( * ) Notice: Subject to any disclaimer, the term of this patent is extended or adjusted under 35 U.S.C. 154(b) by 790 days.

(21) Appl. No.: 11/064,581

(22) Filed: Feb. 24, 2005

(65) Prior Publication Data

US 2006/0185670 A1     Aug. 24, 2006

(51) Int. Cl.
*A61F 13/00* (2006.01)
(52) U.S. Cl. ............... 128/202.12; 604/305; 604/23
(58) Field of Classification Search ........... 128/202.12, 128/205.26; 600/21; 604/23, 289, 290, 293, 604/304, 305, 308
See application file for complete search history.

(56) References Cited

U.S. PATENT DOCUMENTS

| | | | |
|---|---|---|---|
| 871,760 A | 11/1907 | Long et al. |
| 1,117,168 A | 11/1914 | Crowley |
| 3,478,738 A | 11/1969 | Altman et al. |
| 3,602,221 A | 8/1971 | Bleiken |
| 3,669,096 A | 6/1972 | Hurwitz |
| 3,701,349 A | 10/1972 | Larson |
| 3,712,298 A | 1/1973 | Snowden et al. |
| 3,744,491 A | 7/1973 | Fischer |
| 3,785,374 A | 1/1974 | Lipson |
| 3,920,006 A | 11/1975 | Lapidus |
| 3,955,565 A | 5/1976 | Johnson, Jr. |
| 4,003,371 A | 1/1977 | Fischer |
| 4,211,223 A | 7/1980 | LoPiano |
| 4,236,513 A | 12/1980 | LoPiano |
| 4,280,489 A | 7/1981 | Johnson, Jr. |
| 4,328,799 A | 5/1982 | LoPiano |
| 4,331,133 A | 5/1982 | Arkans |
| 4,346,699 A | 8/1982 | Little et al. |
| 4,363,317 A | 12/1982 | Broucek |
| 4,378,009 A | 3/1983 | Rowley et al. |
| 4,628,945 A | 12/1986 | Johnson, Jr. |
| 4,635,635 A | 1/1987 | Robinette-Lehman |
| 4,667,672 A | 5/1987 | Romanowski |
| 4,801,291 A | 1/1989 | Loori |

(Continued)

FOREIGN PATENT DOCUMENTS

WO    WO-2006091243    8/2006

OTHER PUBLICATIONS

Topical Hyperbaric Oxygen Therapy for Lower Extremity Wound Care: An Overview, Podiatry Management, pp. 110-111, Nov. 1997.

(Continued)

*Primary Examiner*—Steven O Douglas
(74) *Attorney, Agent, or Firm*—Lerner, David, Littenberg, Krumholz & Mentlik, LLP

(57) ABSTRACT

A hyperbaric oxygen device and methods of applying hyperbaric oxygen are disclosed. The device comprises an enclosure including a collapsible bag defined by two sheets of fluid impervious material sealed together at both ends such that gas can be delivered between the sheets to inflate the enclosure to a rigid state and maintain the enclosure in the rigid state when oxygen pressure in the interior of the enclosure is cycled between ambient pressure and above ambient pressure.

36 Claims, 8 Drawing Sheets

U.S. PATENT DOCUMENTS

| | | | |
|---|---|---|---|
| 5,029,579 | A | 7/1991 | Trammell |
| 5,060,644 | A | 10/1991 | Loori |
| 5,125,400 | A | 6/1992 | Johnson, Jr. |
| 5,154,697 | A | 10/1992 | Loori |
| 5,234,459 | A | 8/1993 | Lee |
| 5,312,385 | A | 5/1994 | Greco |
| 5,376,067 | A | 12/1994 | Daneshvar |
| 5,437,602 | A | 8/1995 | Polyakov et al. |
| 5,458,562 | A | 10/1995 | Cooper |
| 5,478,310 | A | 12/1995 | Dyson-Cantwell et al. |
| 5,578,055 | A | 11/1996 | McEwen |
| 5,605,534 | A | 2/1997 | Hutchison |
| 5,620,001 | A | 4/1997 | Byrd et al. |
| 5,660,182 | A | 8/1997 | Kuroshaki et al. |
| 5,668,236 | A | 9/1997 | Engelhardt et al. |
| 5,669,390 | A | 9/1997 | McCormick et al. |
| 5,678,543 | A | 10/1997 | Bower |
| 5,738,093 | A | 4/1998 | Santi |
| 5,810,795 | A * | 9/1998 | Westwood .................. 604/305 |
| 5,865,722 | A | 2/1999 | Heng |
| 6,321,746 | B1 | 11/2001 | Schneider et al. |
| 6,622,326 | B2 * | 9/2003 | Richardson ..................... 5/644 |
| 2006/0185670 | A1 | 8/2006 | Loori et al. |

OTHER PUBLICATIONS

The Topical Hyperbaric Oxygen Extremity Chamber, no date.

The Disposable Sacral Topical Hyperbaric Oxygen System, no date.

Dutton, et al. "Topical Hyperbaric Oxygen Therapy: A Case Study" Macassa Lodge, Hamilton, Ontario , (no date).

Heng, et al. "Angiogensis in Necrotic Ulcers Treated with Hyperbaric Oxygen" OstomyWound Management, Sep. 2000, vol. 46, Issue 9. pp. 18-32.

Edsberg. et al. "Use of Topical Hperbaric Oxygen for Treatment of Charonic Wounds in Long-Termn Health Care Facilities" Natural & Health Sciences Research Center, Daemen College, Amherst, NY, (no date).

Edsberg, et al. "Reducing Epibole Using Topical Hyerpbaric Oxygen and Electrical Stimulation" OstomyWound Mangement Apr. 2002, vol. 48, Issue 4, pp. 26-29.

Diamond, et al. "The Effect of Hyperbaric Oxygen on Lower Extremity Ulcerations" Journal of the American Podiatry Association, vol. 72, No. 4, Apr. 1982, p. 180-185.

Lehman, et al. "Human Bite Infections of the Hand: Adjunct Treatment with Hyperbaric Oxygen" Orthopedic Complications, Infections in Surgery , Jun. 1985, pp. 460-465.

Fischer "Topical Hyperbaric Oxygen Treatment of Pressure Sores and Skin Ulcers" reprinted from The Lancet, Aug. 23, 1969, pp.405-409.

Upson "Topical Hyperbaric Oxygenation in the Treatment of Recalcitrant Open Wounds - A clinical report" Physical Therapy, vol. 66, No. 9, Sep. 1986, pp. 1408-1411.

Fischer "Treatment of Ulcers on the Legs with Hyperbaric Oxygen" reprinted from The Journal of Dermatologic Surgery, Inc. vol. 1, No. 3, Oct. 1975, J of Derm Surg 1:3, Oct. 1975, pp. 55-58.

Fries, et al., "Dermal Excisional wound healing in pigs following treatment with topically applied pure oxygen" Mutat Res. 2005 Nov. 11; 579(1-2):172-81. Epub Aug. 18, 2005, Laboratory Molecular Medicine, Dorothy M. Heart and Lung Research Center Institute and Comprehensive Wound Center, Dept. of Surgery, The Ohio State University Medical Center, Columbus, OH, PMID: 16105672 [PubMed—in process], (no date).

Heng "Topical Hyperbaric Therapy for Problem Skin Wounds" J Dermatol Surg Oncol. Aug. 1993; 19(8):784-93, Department of Medicine, UCLA San Fernando Valley Internal Medicine Program, Veterans Administration Medical Center, Sepulveda, PMID: 8349920 [PubMed—indexed for Medline].

Kallianinen, et al. "Topical oxygen as an adjunct to wound healing: a clinical case series" ISP Pathophysiology 9 (2003) 81-87, 2002 Elsevier Science Ireland Ltd.

Heng, et al. "Topical Hyperbaric Therapy for Problem Skin Wounds" 1993 by Elsevier Science Publishing Co., Inc. —0148-0812/93 pp. 784-793.

Kaufman, et al., "Topical oxygen and burn wound healing: a review" Shriners Burns Institute, Cincinnati Unit, Ohio, no date.

Olejniczak, et al. "Topical Oxygen Promotes Healing of Leg Ulcers" Dec. 1976, Medical Times, vol. 104, No. 12, pp. 115-120.

Fries, et al., "Dermal excisional wound healing in pigs following treatment with topically applied pure oxygen" Mutal. Res. Nov. 11, 2005; 579(1-2): 172-81 Epub Aug. 18, 2005, Laboratory of Molecular Medicine, Dorothy M. Davis Heart and Lung Research Institute and Comprehensive Wound Center, Department of Surgery, The Ohio State University Medical Center, Columbus, OH, PMD: 16105672 [PubMed—in process].

Stryker—Taoti Advanced Oxygen Therapy, Inc. Wound Care Solution Excellence, Strategic Discussions Kalamazoo, Michigan, Mar. 21, 2007 powerpoint presentation, 96 pages.

Venous Ulcers Appendix I, Evidence Table per FDA Draft Guidance Document, 8 pages, no date.

Clinical Device Group and the Food and Drug and Law Institute are happy to present: "Getting CMS Reimbursement for Medical Technology Product" 2006, Clinical Device Group, Inc. Powerpoint presentation, 78 pages.

Medical Coverage Advisory Committee, Usual Care of Chronic Wounds, Powerpoint presentation, 144 pages , no date.

CDC Diabetes, Department of Health and Human Services, Centers for Disease Control and Prevention, "National Diabetes Fact Sheet", United States, 2003, General Informationa, 3 pages.

CDC Diabetes, Department of Health and Human Services, Centers for Disease Control and Prevention, "National Estimates on Diabetes", 5 pages., (no date).

Pompeo "The Role of "Wound Burden" in Determining the Costs associated with Wound Care" OstonomyWound Management, Mar. 2001, vol. 47, Issue 3, pp. 65-71.

Frykberg, et al. "Diabetic Foot Disorders: A Clinical Practice Guideline" 2006 revision, The Journal of Foot and Ankle Surgery, vol. 45, No. 5, Sep./Oct. 2006, S1-S66.

American Diabetes Association, "Economic Costs of Diabetes in the U.S. in 2002" Diabetes Care, vol. 26, No. 3, Mar. 2003, pp. 917-932.

Snyder, et al. OstomyWound - Osteomyelitis in the Diabetic Patient: Overview, Diagnosis, Microbiology, "Osteomyelitis in the Diabetic Patient: Diagnosis and Treatment Part 1: Overview, Diagnosis, and Microbiology" (Abstract), no date.

Branom, et al., "Constant Force Technology' versus Low-Air-Loss Therapy in the Treatment of Pressure Ulcers", OstomyWound— Utilizing a Systems Approach to Implement Pressure Ulcer Prediction and Prevention, Sep. 2001, vol. 47, Issue 9, pp. 38-39.

Landau, "Topical hyperbaric oxygen and low energy laser for the treatment of diabetic foot ulcers" Arch. Orthop Trauma Surg (1998) 117: 156-158.

Landau, et al. "Topical hyperbaric oxygen and low energy laser therapy for chronic diabetic foot ulcers resistant to conventional treatment" Yale J. Biol. Med. Mar. -Apr. 2001 74(2):95-100, The Hebrew University, Hadassah School of Medicine, Jerusalem, Israel. PMID: 11393266 [PubMed—indexed for Medline].

Heng, et al. "Angiogenesis in necrotic ulcers treated with hyperbaric oxygen" Department of Medicine, VA Greater Los Angeles healthcare System (Sepulveda), UCLA San Fernando Valley Program, OstomyWound Management, Sep. 2000; 46(9):18-28, 30-2. PMID: 11189538 [PubMed - indexed for Medline].

Sen, et al. "Oxygen, oxidants, and antioxidants in would healing: an emerging paradigm" Laboratory of Molecular Medicine, Dorothy M. Davis Heart and Lung Research Institute, Department of Surgery (CMIS), The Ohio State University Medical Center, Columbus, OH, Ann N.Y. Acad. Sci. 2002 May; 957:239-49, PMID: 12074976 [PubMed - indexed for Medline].

Gordillo, et al. "Revisiting the essential role of oxygen in wound healing" Department of Surgery, Laboratory of Molecular Medicine, 512 Davis Heart and Lung Research Institute, The Ohio State University, 473 West 12th Ave., Columbus, OH, Am. J. Surg. 2003 Sep.; 186(3):259-63, PMID: 12946829 [PubMed—indexed for Medline].

Gordillo, et al. "Revisiting the essential role of oxygen in wound healing" The American Journal of Surgery 186 (2003), pp. 260-263.

Ignacio, et al. "Topical Oxygen Therapy Treatment of Extensive Leg and Foot Ulcers" Journal of the American Podiatric Medical Association, vol. 75, No. 4, Apr. 1985, pp. 196-199.

Cianci "Advances in the treatment of the diabetic foot: Is there a role for adjunctive hyperbaric oxygen therapy?" Wound Repair Regen, Jan.-Feb. 2004; 129(1):2-10, Department of Hyperbaric Medicine, Doctors Medical Center, San Pablo, California, PMID: 14974958 [PubMed— indexed for Medline].

Hopf, et al. "Hyperoxia and angiogenesis" Blackwell Synergy: Wound Repair Regen, vol. 13, Issue 6, pp. 558-564: Hyperoxia and angiogenesis (Abstract); Wound Repair and Regeneration vol. 13 Issue 6 p. 558 - Nov. 2005; http://www.blackwell-synergy.com/doi./abs/10.1111/j.1524-475X.2005.00078.x(1of 3) Dec. 19, 2006.

Kaufman, et al. "The Microclimate Chamber: The Effect of Continuous Topical Administration of 96% Oxygen and 75% Relative Humidity on the Healing Rate of Experimental Deep Burns" The Journal of Trauma, vol. 23, No. 9, pp. 806-815, no date.

Heng, et al. "Endothelial cell toxicity in leg ulcers treated with topical hyperbaric oxygen" Am. J. Dermatopathol 1986 Oct.; 8(5):403-10; MID: 3777378 [PubMed— indexed for Medline].

Heng, et al. "Enhanced Healing and Cost-Effectiveness of Low—Pressure Oxygen Therapy in Healing Necrotic Wounds: A feasibility study of technology transfer" Ostomy/Wound Management 2000; 46(3):52-62; From the Division of Dermatology, Department of Medicine, Department of Veterans Affairs, VAGLAHS (Sepulveda), UCLA San Fernando Valley Program, pp. 52-60.

Harkless, et al. "Seven keys to Treating Chronic Wounds" Diabetes Watch, Podiatry Today, Dec. 2000, pp. 17-19.

Diabetes Care, published by the American Diabetes Association "Study Finds Diabetes Will Double in World by 2030: Predicts Rapid U.S. increase That Greatly Exceeds Prior CDC Projections" lead author Dr. Sarah Wild, Public Health Sciences, University of Edinburgh, 2 pages, no date.

Clinical Device Group, Evaluations for Medical Devices, "Q&A Session for Getting CMS Reimbursement for Medical Technology Products", Sep. 7, 2006.

Rossi, Hudson Podiatry Center Letter, no date.

* cited by examiner

HYPERBARIC OXYGEN DEVICES AND DELIVERY METHODS

FIELD OF THE INVENTION

This invention relates to hyperbaric oxygen delivery devices and methods.

BACKGROUND

The use of oxygen for treatment of open wounds and sores has long been understood to have practical medical application as a supplement or replacement to conventional antibiotic therapy. Oxygen is believed to be bactericidal to the anaerobic bacteria that tend to grow in both open and closed wounds. Application of oxygen to wounds under pressure is known in the art as hyperbaric treatment. It has been shown that varying the pressure of such oxygen treatment, increases blood circulation in the treated area. This has the added advantage of pumping the patient's blood to the extremity such that the patient's own white blood cells are better able to assist in treatment of the microbes present in the wound or sore.

There are generally two broad general categories of devices for administering hyperbaric oxygen to a patient. The first category includes larger devices designed to enclose a patient's entire body or large portion of a patient's body, for example, both of the lower extremities of a patient. A second category of devices includes smaller, portable devices, which are known in the art as topical hyperbaric chambers and enclose a local region of the patient's body such as a single leg or a single arm.

There are several different devices used to apply topical oxygen to a patient's open wounds or sores. Certain existing hyperbaric oxygen devices include a rigid plastic enclosure that proves a pure oxygen atmosphere around the wound. Another characteristic of certain existing devices is that the oxygen is applied at a pressure greater than ambient pressure up to a maximum allowable level of fifty millimeters of mercury above ambient pressure. In one type of device, oxygen is applied to an entire extremity, for example, a leg having a wound or sore on a portion of the leg.

Various topical hyperbaric devices utilize a flexible bag designed to cover an entire leg or other extremity. Typically, these disposable hyperbaric oxygen chambers include a polyethylene bag which is substantially the length of the patient's leg, and tape is used at the top of the bag to seal the chamber around the upper thigh. Some hyperbaric oxygen chambers are in the form of an inflatable single layer bag, in which the pressure of oxygen is pulsated between minimum and maximum values, however, a disadvantage associated with a single layer bag is that during pulsated delivery of oxygen, the bag has a tendency to collapse when the pressure is reduced in the bag. Collapse of the bag poses the risk of the bag contacting the wound on the treated extremity. It would be desirable to provide a hyperbaric oxygen chamber that could be used to treat a single extremity and does not collapse when the pressure of the oxygen in the bag is reduced during pulsated delivery therein.

SUMMARY OF THE INVENTION

According to a first aspect of the invention, a topical hyperbaric device is provided, which comprises an enclosure including an interior and an exterior, the enclosure closed on one end and open on the other end and sized and shaped to receive a patient's extremity, the enclosure defined by a collapsible bag including two sheets of fluid impervious material sealed together at both ends, a first side of one sheet defining the exterior of the enclosure, a first side of the other sheet defining the interior of the enclosure such that gas can be delivered between the sheets to inflate the enclosure to a substantially rigid condition and maintain the enclosure in the substantially rigid condition when oxygen pressure in the interior of the enclosure is cycled between first and second pressures, e.g., at least about ambient pressure and above ambient pressure.

In some embodiments, the device further comprises seal proximate the open end of the enclosure adapted to establish contact between the patient's extremity to prevent oxygen from escaping from the enclosure. In certain embodiments, the seal may include an inflatable cuff. In other embodiments, the seal comprises a strap wrapped around the patient's extremity.

Another aspect of the invention pertains to a method of treating an extremity of a patient with hyperbaric oxygen comprising placing a collapsible bag having an open end and a closed end in a substantially rigid state defining a chamber adapted to receive a patients extremity; inserting a patient's extremity through the open end of the chamber; sealing the chamber around the patient's extremity to prevent gas delivered to the interior of the chamber from escaping; and delivering oxygen to the interior of the chamber. In certain embodiments, the method further comprises cycling the pressure in the interior of the chamber between ambient pressure and above ambient pressure, wherein the bag remains in a rigid state during the entire cycle. In other embodiments, sealing the chamber around the patient's extremity includes inflating an inflatable cuff located proximate the open end of the bag.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS

Before describing several exemplary embodiments of the invention, it is to be understood that the invention is not limited to the details of construction or process steps set forth in the following description. The invention is capable of other embodiments and of being practiced or carried out in various ways.

The present invention pertains to hyperbaric oxygen delivery devices and methods. According to one or more embodiments, although the oxygen therapy device may be used to treat various body parts, including, but not limited to arms, hands, feet, and legs, according to certain embodiments, the devices are particularly suitable for treatment of a patient's leg. The various features and advantages of the oxygen delivery device will become more apparent from the following detailed description taken in conjunction with the accompanying drawings.

Figure 1:
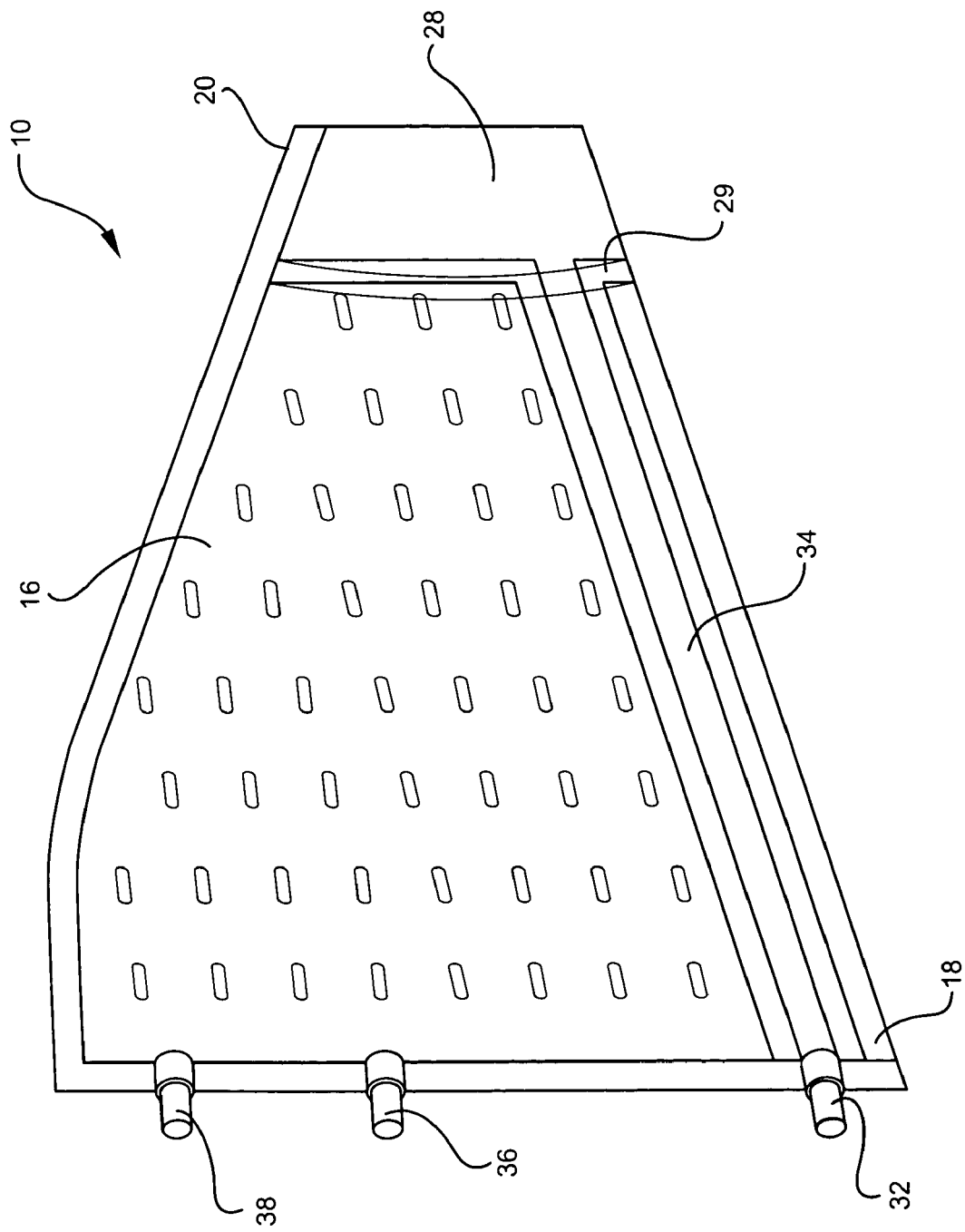
FIG. 1 is a perspective view of a hyperbaric oxygen device in a deflated condition according to one embodiment of the present invention.
Figure 2:
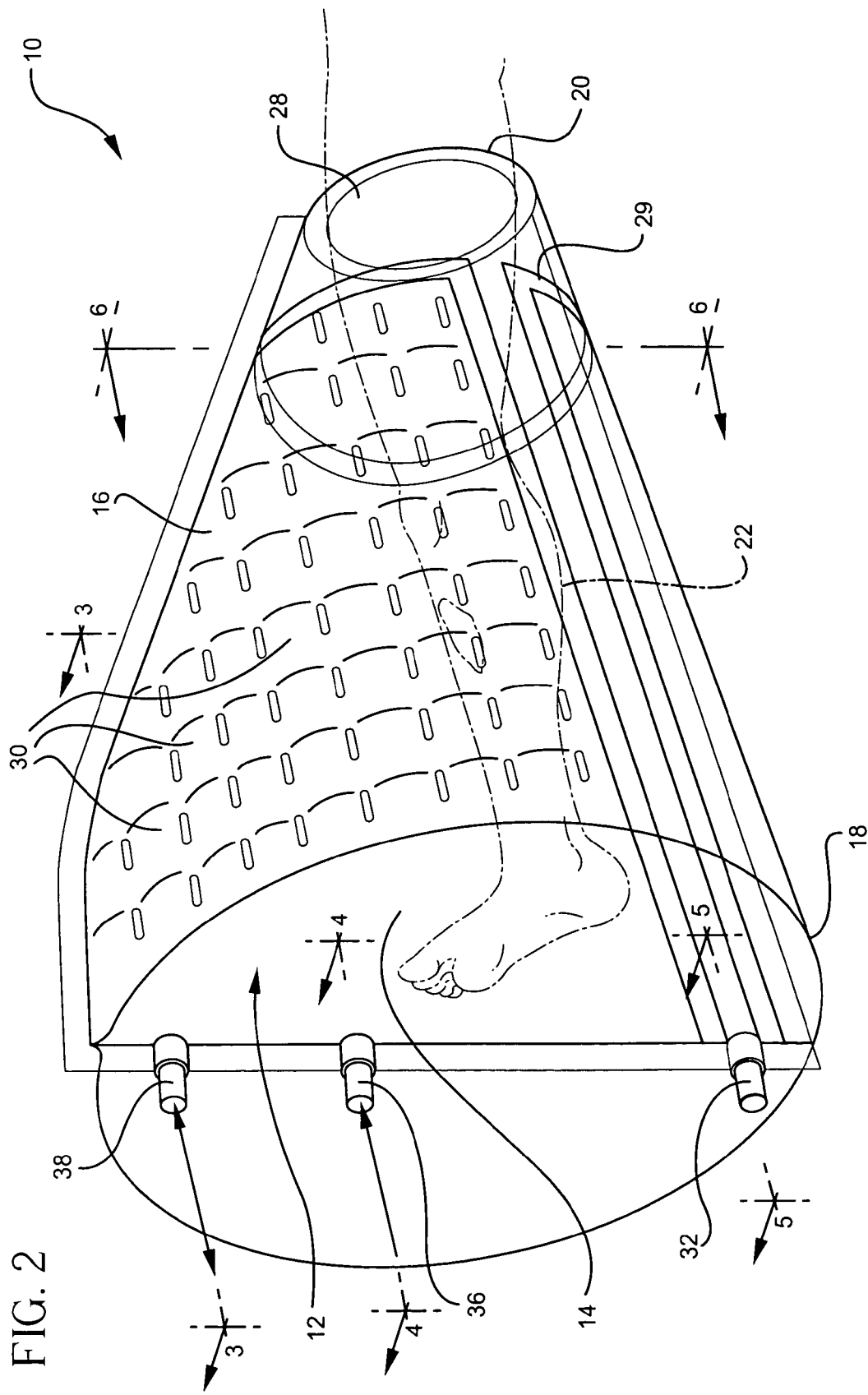
FIG. 2 is a perspective view of the device shown in FIG. 1 in an inflated condition.
Figure 3:
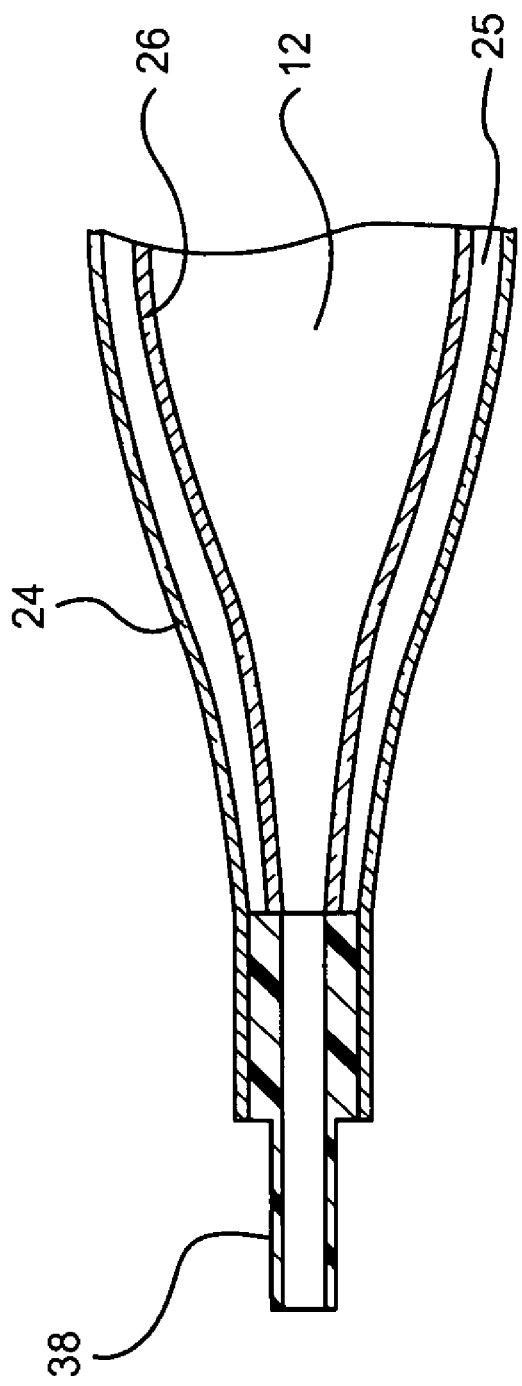
FIG. 3 is a cross-sectional view taken along line 3-3 of FIG. 2.

Referring now to the Figures, and in particular, FIGS. 1-6, an oxygen delivery device is shown according to an embodiment of the invention. FIGS. 1 and 2 show a topical hyperbaric device 10, which comprises an enclosure 12 including an interior 14 and an exterior 16. The enclosure 12 is closed on one end 18 and open on the other end 20 and sized and shaped to define a main chamber which can receive a patient's extremity, for example, a leg 22 as shown in FIG. 3. The enclosure 12 shown in FIGS. 1 and 2 is defined by a collapsible bag including at least two sheets, an outer sheet 24, and an inner sheet 26 defining a space 25 therebetween. It will be understood that the bag defining the enclosure 12 can include two sheets or a greater number of sheets sealed together to define the enclosure 12. For example, the bag can be formed by four sheets (not shown) of material, two inner sheets and two outer sheets, stacked and sealed together at the ends 18, 20 and the edges connecting the ends. A bag made from four sheets would provide an enclosure with an interior, the interior bounded by the inner sheets of material, the outer sheets of material defining the exterior of the enclosure, and a space between the outer sheets and the inner sheets.

The sheets 24, 26 are made of fluid impervious material sealed together at both ends 18, 20 of the enclosure so that that gas can be delivered to a space 25 between the sheets 24, 26 to inflate the bag to a rigid state and maintain the bag in the rigid state when oxygen pressure in the interior of the enclosure is cycled between ambient pressure and above ambient pressure. In certain embodiments, the sheets of material are a resinous material such as polyethylene, however, the present invention is not limited to a particular type of material. As is known in the art of hyperbaric oxygen delivery, hyperbaric oxygen therapy may involve the pulsed delivery of oxygen in which the pressure of oxygen inside the enclosure is cycled between at least about atmospheric or ambient pressure to a pressure up to 50 mm of mercury above atmospheric or ambient pressure. As will be described further below, the structure of the collapsible and flexible hyperbaric oxygen device permits the device to be inflated to a rigid state so that the bag does not collapse and contact the wounded portion of the patient's extremity during pulsed oxygen delivery when the pressure of the oxygen inside the enclosure is reduced to atmospheric pressure.

Figure 6:
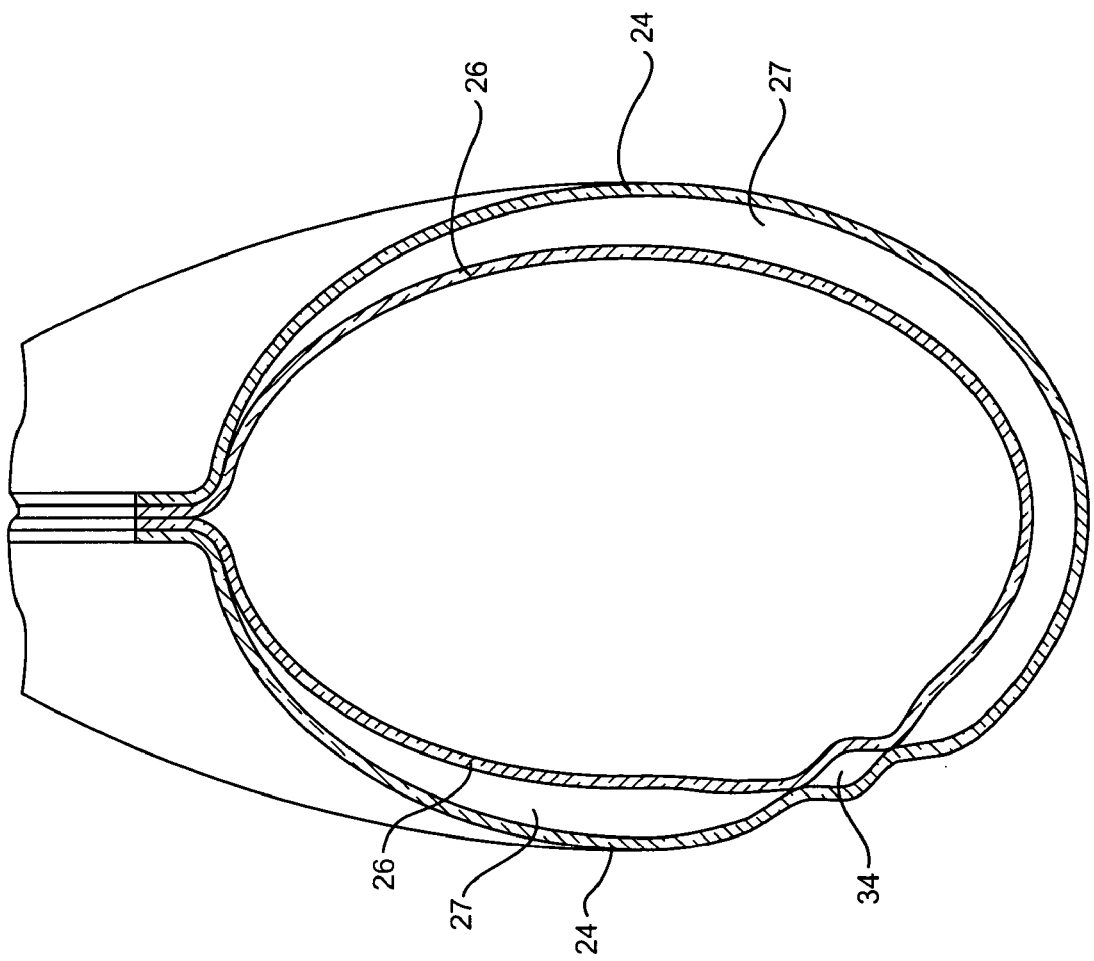
FIG. 6 is a partial cross-sectional view taken along line 6-6 of FIG. 2.

The device shown in FIGS. 1 and 3 further comprises a seal proximate the open end 20 of the enclosure adapted to establish contact between the patient's extremity to prevent oxygen from escaping from the enclosure. As best shown in FIGS. 2 and 6, the seal can comprise an inflatable cuff 28 that surrounds the patient's extremity 22 during the oxygen treatment and forms a substantially fluid tight seal around the extremity. As shown in the Figure, the cuff 28 is defined by a first seal line 29 in which the sheets of material are sealed together adjacent the open end 18 of the device and the terminal end of the device where the sheets of material are sealed together. As will be described in more detail below, the cuff is defined by the outer sheet 24, the inner sheet 26 and a cuff space 27 between the sheets 24, 26. The cuff space 27 increases as gas is delivered to the space to inflate the cuff 28. In the embodiment shown, the inflatable cuff is formed integrally with the enclosure 12 and is disposed between the sheets 24, 26 of material.

The device may further comprise a plurality of interconnected pockets 30 or miniature chambers formed between the sheets 24, 26. The pockets can be formed by securing portions of the sheets of material together at selected, discrete locations. The sheets can be secured together at selected portions by any suitable means, such as by adhesively sealing the sheets together, heat sealing, or ultrasonically welding the sheet together at selected, discrete points in an array resembling a waffle pattern. The present invention is not limited to a particular pattern for forming the interconnected pockets 30, and other patterns are within the scope of the invention.

In the embodiment shown in FIGS. 1-6 in which the seal includes an inflatable cuff 28, the device further comprises a first fluid port 32 in communication with the cuff. The first fluid port 32 may be located adjacent to the closed end 18 of the device and may be in communication with a channel 34 in fluid communication with the cuff space 27. The channel 34 may be defined by a space between the inner sheet 26 of material, and the outer sheet of material that defines the enclosure can be eliminated at this area of the bag that defines the channel. Alternatively, the channel can be defined by a hose or other suitable structure in fluid communication with the cuff space 27. It will be understood that the first fluid port 32 does not necessarily have to be connected to the cuff space 27 in the manner shown. In alternative embodiments, the first fluid port 32 may be adjacent the open end 20 and more directly connected to the cuff space 27.

Figure 4:
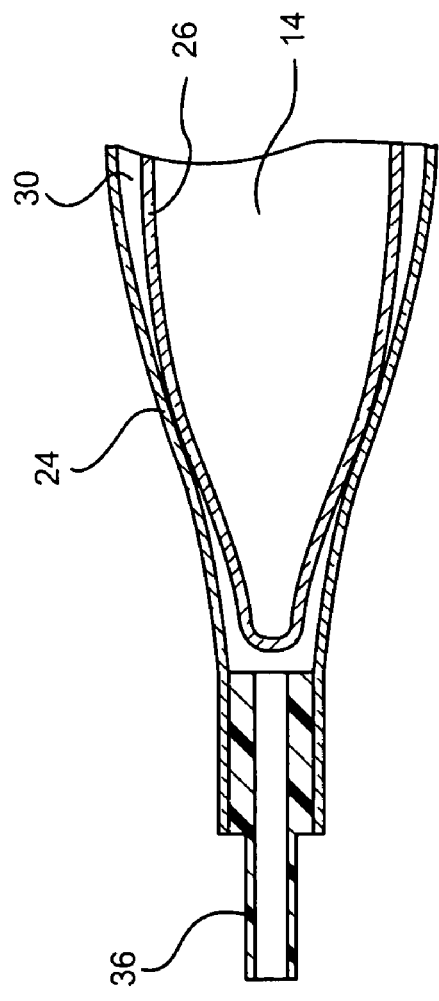
FIG. 4 is a cross-sectional view taken along line 4-4 of FIG. 2.
Figure 5:
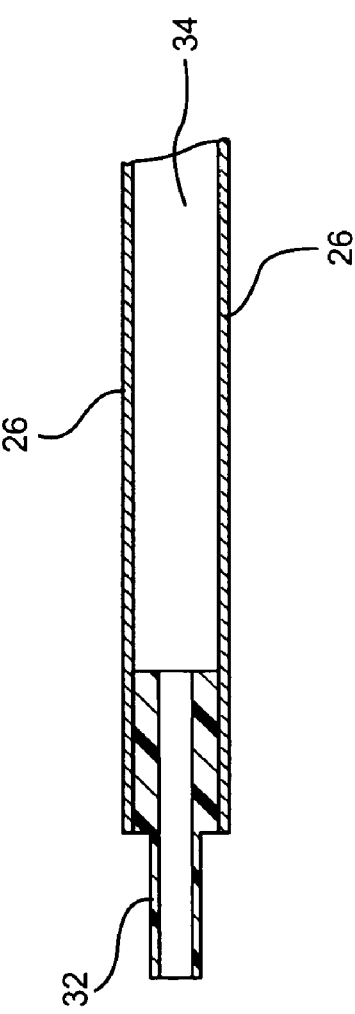
FIG. 5 is a cross-sectional view taken along line 5-5 of FIG. 2.

Referring now to FIGS. 2 and 4, the device may further comprise a second fluid port 36 in communication with the interconnected pockets 30. As shown in FIGS. 2 and 4, gas can be introduced into the second fluid port 36 and the gas will inflate the space between the inner sheet 26 and outer sheet 24 and fill the interconnected pockets 30. Gas is introduced until the pockets 30 are all filled and the device is inflated to the point that the device is in a substantially rigid state, similar to an air mattress. In addition, inflating the pockets so that the device is in the substantially rigid condition provides an enclosure sized and shaped to hold a patient's extremity, for example, a leg 22.

Figure 8:
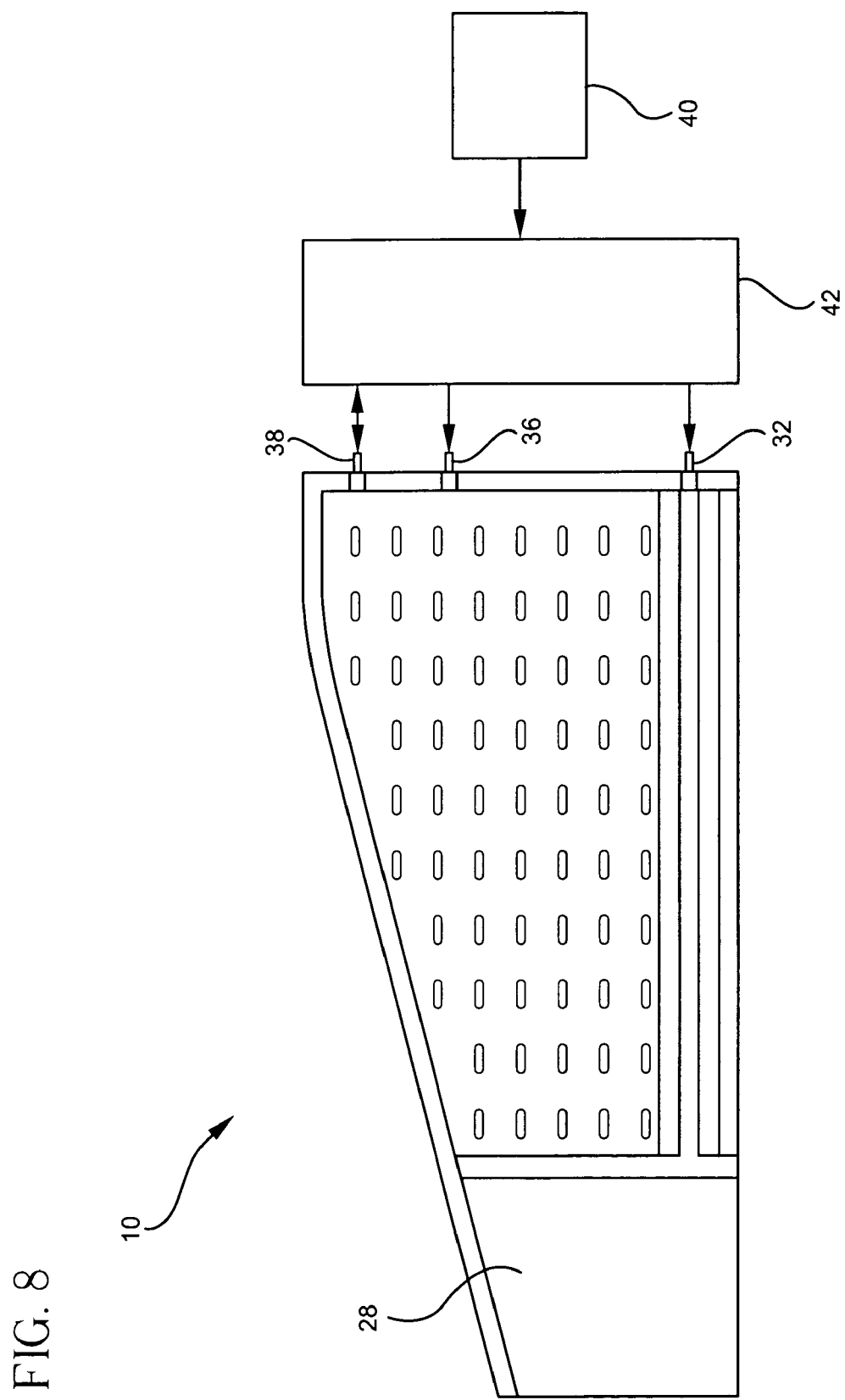
FIG. 8 is a top view of the device shown in FIG. 1 together with a system for delivering oxygen to the device of FIG. 1.

The device may further comprise a third fluid port 38 (shown in FIGS. 2 and 3) in communication with the interior of the enclosure 12. Referring now to FIG. 8, the each of the fluid ports 32, 36, and 38 can be connected to a gas supply 40, which is connected to a controller 42 for regulating the delivery of gas to the fluid ports. The controller 42 is operable to control the pressure and rate of delivery of the gas to each of the ports. In certain embodiments, oxygen is delivered to all three fluid ports. In other embodiments, air or another gas may be delivered to fluid ports 32 and 36 for inflating the cuff 28 and the interconnected pockets.

Figure 7:
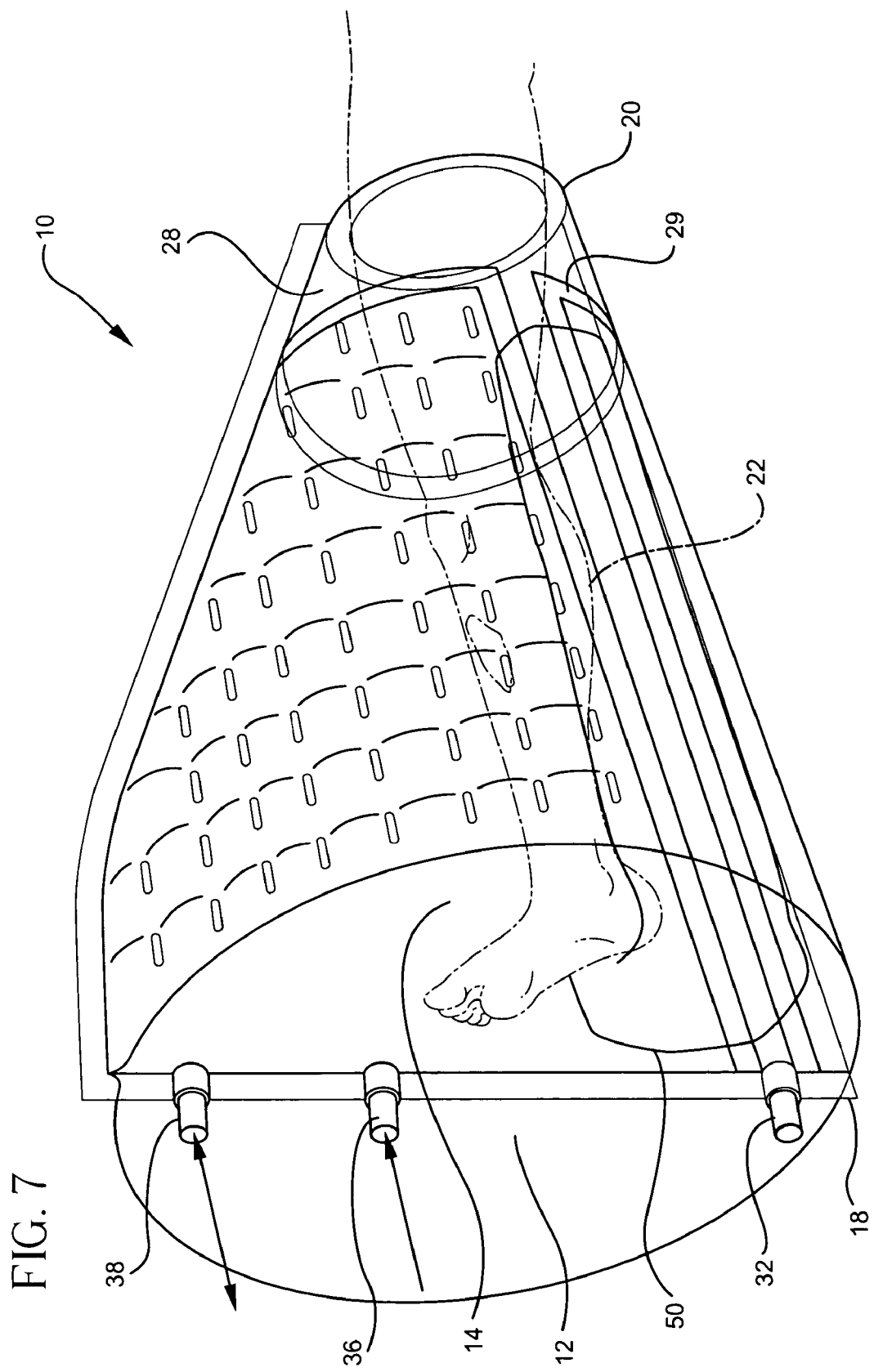
FIG. 7 is a perspective view of a hyperbaric oxygen device in an inflated condition according to another embodiment of the invention.

Referring now to FIG. 7, another embodiment of the invention relates to a hyperbaric chamber having essentially all of the same components shown and described in FIGS. 1-6 and in which like reference numerals are used for similar elements. The device 10 may further include an inflatable pillow 50 contained within the interior 14 of the enclosure 12. The pillow may be formed integrally in the interior of the chamber, and a separate fluid port (not shown) or fluid port 32 can be routed to the pillow so that the pillow 50 can be inflated.

Figure 9:
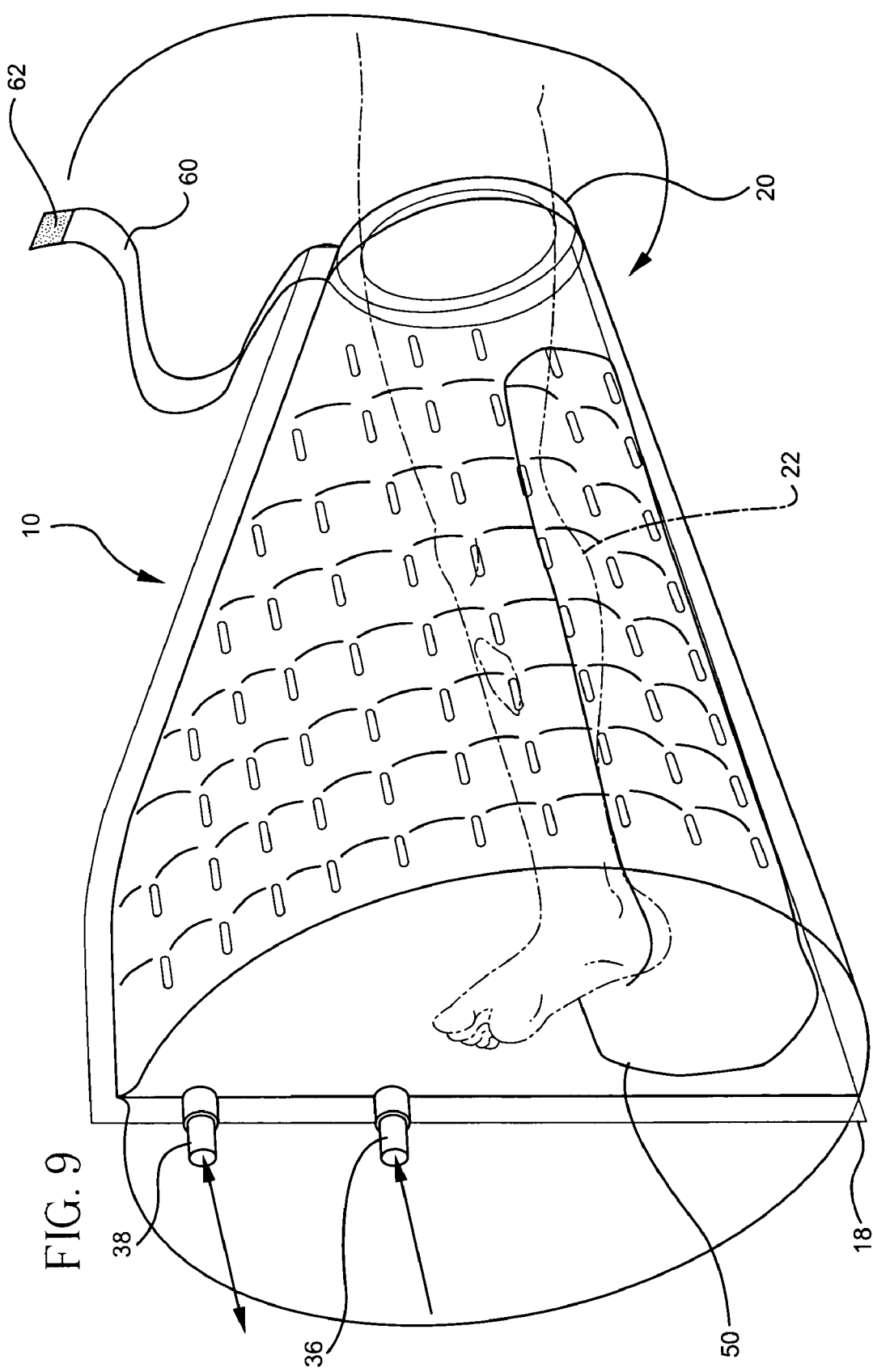
FIG. 9 is a perspective view of a hyperbaric oxygen device in an inflated condition according to another embodiment of the invention.

FIG. 9 shows still another embodiment of a hyperbaric chamber 10, again in which like reference numerals depict elements that are similar to the previously described embodiments. In the embodiment shown in FIG. 9, the seal on the open end 20 of the device 10 is defined by a strap 60, which can be integrally formed with the plastic sheets that make up the enclosure that can be secured to the device 10. The strap 60 is an appropriate length to wrap around the patient's extremity 22 at least once, and in certain embodiments the strap is sized to wrap around the patient's extremity 22 at least two times. The strap 60 may include an adhesive portion 62, which includes an adhesive or other suitable material for securing the strap 60 to the device 10 to provide a substantially gas tight seal. It will be appreciated that in this embodiment, the first fluid port 32 for inflating a cuff can be eliminated as shown in FIG. 9, or alternatively, the first fluid port 32 can be routed and placed in fluid communication with the pillow 50.

Another aspect of the invention pertains to a method of treating an extremity of a patient with hyperbaric oxygen. The method comprises placing a collapsible bag of the type shown in the Figures having an open end and a closed end in a rigid state defining a chamber adapted to receive a patients extremity, inserting a patient's extremity through the open end of the chamber; sealing the chamber around the patient's extremity to prevent gas delivered to the interior of the chamber from escaping, and delivering oxygen to the interior of the chamber. The method may further comprise cycling the pressure in the interior the chamber between ambient pressure and above ambient pressure, wherein the bag remains in a rigid state during the entire cycle. It is preferred that the interior of the chamber does not contact the patient's leg during delivery of the oxygen to the extremity. The pressure may be cycled up to a pressure of about 50 mm of mercury above at least atmospheric pressure, as is known in the art of hyperbaric oxygen treatment.

All dressings and ointments should be removed from the patient's extremity prior to the hyperbaric oxygen treatment. The patient's extremity may be placed on a foam carrier. Alternatively, in embodiments in which the device includes an inflatable pillow, the pillow will be inflated, and the main chamber of the device will be inflated until the device is in a rigid state. In preferred embodiments, the device assumes a round, tubular configuration, but the present invention is not limited to any particularly shaped device. After the device has been inflated to a rigid state, the patient's extremity is introduced into the chamber by either sliding the foam lined carrier into the chamber, or inserting the patient's leg through the open end of the chamber and resting it on the inflatable pillow.

A seal is then formed at the open end of the device. The seal may be achieved by inflation of the cuff or wrapping the strap around the patient's leg, or an alternative sealing means may be used ensure a good seal between the leg and the flexible chamber. Oxygen is then introduced into the chamber up to a maximum pressure of 50 mm of mercury above atmospheric pressure. It is desirable to now pulsate the flow of oxygen to that it builds to a maximum pressure, less than or equal to 50 mm of mercury and then dropping to a low of at least about ambient or atmospheric pressure, for example, five inches of mercury above ambient, with a cycle time of less than about one minute. This cycle is then repeated during the course of therapy that is typically one to two hours in duration.

According to one or more embodiments of the present invention, inflation of the device keeps the chamber wall off the sensitive wound. This makes the use of the device more comfortable for the patient and reduces the chance of biological contamination. Previous flexible designs do not employ this feature, and employment of pulsating therapy in previous flexible designs would result in collapse of the device around the patient's extremity due to lack of rigid walls. According to one or more embodiments of the present invention, the device can be easily stowed away or disposed of after use. Another advantage over the previous rigid hyperbaric chambers is that it is possible to bend this device to fit legs that could not have been previously placed in a rigid chamber.

Fabrication of the flexible chamber can include using known methods of heat bonding or radio frequency welding to make the seams or joints. Various combinations of polyethylene have been found to be suitable in the construction of the device. Obviously, many other modifications and alterations of this invention will occur to those with ordinary skill. Accordingly, the present invention should be limited only to the spirit and scope of all hyperbaric treatment devices that utilize air erected walls in order to construct the oxygen therapy chamber.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims and their equivalents.

The invention claimed is:

1. A device for delivering treatment gas to an extremity of a patient comprising:
an enclosure including an interior and an exterior, the enclosure closed on one end and open on the other end and sized and shaped to receive the patient's extremity, the enclosure defined by a collapsible bag including two sheets of fluid impervious material sealed together, a first side of one sheet defining the exterior of the enclosure, a first side of the other sheet defining the interior of the enclosure, the sheets further forming a plurality of pockets such that gas can be delivered to the pockets to inflate and maintain the enclosure in a substantially rigid condition when treatment gas pressure in the interior of the enclosure is cycled between first and second pressures.

2. The device of claim 1, further comprising a seal proximate the open end of the enclosure adapted to establish contact between the patient's extremity to prevent treatment gas from escaping from the enclosure.

3. The device of claim 2, wherein the seal comprises an inflatable cuff.

4. The device of claim 3, wherein the inflatable cuff is formed integrally with the enclosure.

5. The device of claim 4, wherein the inflatable cuff is defined by at least two sheets of material.

6. The device of claim 1, wherein the seal comprises a strap.

7. The device of claim 6, wherein the strap includes an adhesive portion.

8. The device of claim 1, wherein the pockets are interconnected.

9. The device of claim 8, wherein the pockets are formed by securing portions of the sheets of material together.

10. The device of claim 1, further comprising an inflatable pillow contained with the interior of the enclosure.

11. The device of claim 10, wherein the pillow is formed integrally with one of the sheets of material.

12. The device of claim 1, wherein the sheets of material are a resinous material.

13. The device of claim 12, wherein the resinous material includes polyethylene.

14. The device of claim 3, further comprising a first fluid port in communication with the cuff.

15. The device of claim 14, further comprising a second fluid port in communication with the interconnected pockets.

16. The device of claim 15, further comprising a third fluid port in communication with the interior of the enclosure.

17. The device of claim 16, wherein the fluid ports are connected to a gas supply.

18. The device of claim 17, wherein the fluid ports are connected to a controller for regulating the pressure of gas.

19. A wound treatment device comprising:
a main chamber adapted to receive a treatment fluid defined by a collapsible bag comprising a sheet of fluid impervious material, the bag being sealed on a first end and being open on a second end, the main chamber sized and shaped to enclose a patient's extremity;
an inflatable cuff proximate the open end of the chamber for sealing the main chamber around the patient's extremity; and
means for retaining the collapsible bag in a rigid state, the means comprising a plurality of inflatable secondary chambers at least partially surrounding said main chamber, such that the sheet forming the main chamber when said secondary chambers are maintained under a fluid pressure, does not contact the patient's wound when said treatment fluid is cycled between first and second pressures within said main chamber.

20. A method of treating an extremity of a patient with treatment gas comprising:
providing a collapsible bag having an open end, a closed end, and a chamber defined therebetween adapted to receive a patient's extremity, the bag further comprising a wall having a plurality of inflatable pockets;
rigidifying the wall by inflating the pockets with a fluid;
inserting a patient's extremity through the open end of the bag;
sealing the open end around the patient's extremity to prevent treatment gas delivered to the chamber from escaping; and
delivering treatment gas to the chamber in a pulsed manner between first and second pressures, wherein the bag remains in a substantially rigid state and does not collapse around the patient's extremity.

21. The method of claim 20, wherein the wall comprises a double-layer of fluid impervious material and a space therebetween.

22. The method of claim 20, wherein the plurality of pockets are formed between two sheets of material forming the wall and wherein the pockets are interconnected.

23. The method of claim 20, wherein sealing the open end around the patient's extremity includes inflating an inflatable cuff located proximate the open end of the bag.

24. The method of claim 20, wherein sealing the chamber around the patient's extremity includes wrapping an integral strap around the patients leg.

25. A wound treatment device for delivering treatment gas to a wound, said device comprising:
a collapsible flexible cover, the cover forming a wall configured to form a chamber for placement over a wound, the wall further configured to be substantially rigid when forming the chamber independent of pressure in the chamber, said wall being substantially gas impermeable for facing the wound when the cover is placed over the wound, wherein said wall includes a plurality of inflatable pockets that upon being inflated rigidify the wall; and
an inlet in communication with the chamber for delivering treatment gas into the chamber.

26. A wound treatment device for delivering treatment gas to a wound, said device comprising:
a flexible cover, the cover having a wall with a plurality of inflatable pockets to rigidify the cover when inflated, the wall having a separate first side and a separate second side, wherein the second side is substantially gas impermeable for facing a wound when the cover is placed over the wound and for forming a chamber over the wound;
a source of treatment gas;
a controller; and
an inlet in fluid communication with the chamber and the source of treatment gas for delivering treatment gas into the chamber, the controller varying the flow of treatment gas into the chamber to thereby vary the pressure of the treatment gas in the chamber.

27. The device of claim 26, further comprising the wall having a separate first side and a separate second side.

28. The device of claim 27, wherein the first side is coupled to the second side at a portion thereof.

29. The device of claim 27, wherein the first and second sides are coupled together at a plurality of points, thereby creating the pockets.

30. The device of claim 29, wherein the pockets are configured to receive a gas.

31. The device of claim 28, wherein the first and second sides are coupled together by adhesive, heat, or ultrasonic welding.

32. A wound treatment device for delivering treatment gas to a wound, said device comprising:
a chamber wall defining a main chamber and a plurality of inflatable secondary chambers, the secondary chambers being inflatable between deflated state wherein the chamber wall is collapsible and an inflated state wherein the chamber wall becomes at least partially rigid thereby defining the chamber for placement about a wound, the chamber wall being spaced from the wound; and
an inlet in communication with the chamber for delivering treatment gas into the chamber.

33. The device of claim 32, wherein the chamber wall comprises a first sheet and a second sheet.

34. The device of claim 33, wherein the first and second sheets are coupled together at a plurality of points.

35. The device of claim 33, wherein the first sheet is gas impermeable.

36. The method of claim 1, wherein the treatment gas is oxygen.

* * * * *